(12) United States Patent
Goskonda et al.

(10) Patent No.: US 9,345,771 B2
(45) Date of Patent: *May 24, 2016

(54) ORAL CANNABINOID FORMULATIONS

(71) Applicant: Insys Therapeutics, Inc., Phoenix, AZ (US)

(72) Inventors: Venkat R. Goskonda, Phoenix, AZ (US); Ashok Chavan, Chandler, AZ (US); Amit Kokate, Englewood, NJ (US); Howard Gill, Scottsdale, AZ (US)

(73) Assignee: INSYS DEVELOPMENT COMPANY, INC., Chandler, AZ (US)

( * ) Notice: Subject to any disclaimer, the term of this patent is extended or adjusted under 35 U.S.C. 154(b) by 65 days.

This patent is subject to a terminal disclaimer.

(21) Appl. No.: 13/644,283

(22) Filed: Oct. 4, 2012

(65) Prior Publication Data

US 2014/0100269 A1   Apr. 10, 2014

(51) Int. Cl.
*A61K 47/10* (2006.01)
*A61K 9/00* (2006.01)
*A61K 31/353* (2006.01)

(52) U.S. Cl.
CPC .............. *A61K 47/10* (2013.01); *A61K 9/0095* (2013.01); *A61K 31/353* (2013.01)

(58) Field of Classification Search
None
See application file for complete search history.

(56) References Cited

U.S. PATENT DOCUMENTS

| | | | |
|---|---|---|---|
| 6,509,005 B1 | 1/2003 | Peart et al. | |
| 6,747,058 B1 * | 6/2004 | Dedhiya et al. | 514/454 |
| 7,025,992 B2 | 4/2006 | Whittle et al. | |
| 7,709,536 B2 | 5/2010 | Whittle | |
| 8,222,292 B2 * | 7/2012 | Goskonda et al. | 514/454 |
| 2003/0191180 A1 | 10/2003 | Ross | |
| 2004/0110828 A1 | 6/2004 | Chowdhury, II et al. | |
| 2004/0162336 A1 * | 8/2004 | McPhillips et al. | 514/454 |
| 2004/0229939 A1 | 11/2004 | Chowdhury, II et al. | |
| 2005/0079136 A1 | 4/2005 | Woolfe et al. | |
| 2006/0258738 A1 | 11/2006 | Dieterich | |
| 2007/0049645 A1 | 3/2007 | Mechoulam et al. | |
| 2007/0060639 A1 | 3/2007 | Wermeling | |
| 2007/0072939 A1 | 3/2007 | Kupper | |
| 2007/0099987 A1 | 5/2007 | Weiss et al. | |
| 2007/0104741 A1 | 5/2007 | Murty et al. | |
| 2008/0112895 A1 * | 5/2008 | Kottayil et al. | 424/46 |

OTHER PUBLICATIONS

Ruckenstein et al., "Solubility of drugs in aqueous solutions part 3: multicomponent mixed solvent", Science Direct, International Journal of Pharmaceuticals, 267, 2003, pp. 121-127.

Anderson et al., "Excipients for oral liquid formulations", Taylor & Francis Group, LLC., 2006, pp. 151-180.

Nicholson et al., "Effect of a Δ-9-tetrahydrocannabinol and cannabidiol on nocturnal sleep and early-morning behavior in young adults", Journal of Clinical Psychopharmacology, vol. 24, No. 3, Jun. 2004, pp. 305-313.

GW Pharm Ltd., "Named SATIVEX physician product information", Mar. 14, 2007, pp. 1-10.

* cited by examiner

*Primary Examiner* — Jeffrey S Lundgren
*Assistant Examiner* — William Lee
(74) *Attorney, Agent, or Firm* — Wood, Phillips, Katz, Clark & Mortimer

(57) ABSTRACT

Oral cannabinoid formulations, including an aqueous-based oral dronabinol solution, that are stable at room or refrigerated temperatures and may possess improved in vivo absorption profiles with faster onset and lower inter-subject variability.

12 Claims, No Drawings

ORAL CANNABINOID FORMULATIONS

FIELD OF INVENTION

The present invention relates to an aqueous-based oral cannabinoid solution comprising water, alcohol and propylene glycol that is stable at room or refrigerated temperatures and has an improved in vivo absorption profile with faster onset and lower inter-subject variability when compared with current gelatin capsule cannabinoid formulations.

BACKGROUND OF THE INVENTION

Delta-9-Tetrahydrocannabinol (also known as THC, dronabinol and D9THC) is a naturally occurring compound and is the primary active ingredient in the controlled substance marijuana. Marijuana refers to the dried flowers and leaves of *Cannabis Sativa*, the hemp plant. These parts of the plant contain several compounds called cannabinoids (including dronabinol), that may help patients with certain disease conditions. Dronabinol has been approved by the Food and Drug Administration (FDA) for the control of nausea and vomiting associated with chemotherapy and, more recently, for appetite stimulation of AIDS patients suffering from wasting syndrome. Synthetic dronabinol has been utilized as a pharmaceutically active ingredient, and *cannabis*-based medicines using botanical sources of *cannabis* rather than synthetic THC are also known in the art.

Despite all of the work on cannabinoids and dronabinol outlined above and elsewhere, to date a solution formulation of a cannabinoid, such as an aqueous-based oral dronabinol solution, has not been achieved that is stable at room or refrigerated temperatures and that has an improved in vivo absorption profile with faster onset and lower inter-subject variability than currently available dronabinol gelatin capsules.

SUMMARY OF THE INVENTION

The present invention is directed to liquid cannabinoid formulations, and more particularly to an aqueous-based oral cannabinoid solution comprising water, alcohol and propylene glycol that is stable at room or refrigerated temperatures and possesses an improved in vivo absorption profile, with lower inter-subject variability, over existing oral cannabinoid formulations.

All percentages of ingredients reported herein are expressed as weight by weight, unless otherwise indicated.

It is a further object of the invention to provide formulations comprising a cannabinoid, preferably, dronabinol, and the following ingredients: (i) from about 0 to about 40% water, (ii) from about 15 to about 65% alcohol, preferably ethanol, and (iii) a co-solvent that is (a) propylene glycol from about 0% to about 50%, (b) polyethylene glycol from about 0 to about 50%, and/or (c) a combination of (a) and (b), the solution having a combined total of 100%, wherein the formulations are suitable for oral administration and have in vivo absorption variability of less than 50%.

In other embodiments, the provided formulations contain between about 25% to about 33% w/w water; more preferably, between about 30% and about 33% w/w water.

In yet other embodiments, the provided formulations contain about 50% w/w alcohol.

In yet other embodiments, the provided formulations contain between about 5% to about 21% w/w a co-solvent.

In yet other embodiments, the provided formulations contain between about 0.1% to about 5% w/w dronabinol.

In yet other embodiments, the provided formulations contain about 5.5% w/w propylene glycol and about 12% w/w polyethylene glycol.

In other embodiments, the provided formulations further include butylated hydroxyanisole (BHA) in amount of about 0.01% w/w.

In all embodiments, the combined total of all ingredients is 100%.

In a preferred embodiment, the invention provides an oral pharmaceutical solution comprising about 0.54% w/w dronabinol, about 31.9% w/w water, about 12% w/w polyethylene glycol, about 5.5% w/w propylene glycol, about 0.01% w/w BHA, about 0.05% w/w sucralose, and about 50% w/w alcohol.

It is a still further object of the invention to provide methods of treatment wherein the cannabinoid formulations are suitable for administration by the delivery route selected from the group consisting of: intrapulmonary, oral, transmucosal (eg. buccal and sublingual), transdermal, intravenous and ophthalmic.

In certain preferred embodiments, the present invention provides an aqueous cannabinoid formulation (e.g., dronabinol) that is stable at all conditions-refrigerated, cool and room temperature. In other words, in certain preferred embodiments, the stabilized aqueous cannabinoid formulations may be stored at ambient temperature and humidity, or in a refrigerator, by the patient.

In certain embodiments, formulations and methods of the invention provide for the active pharmaceutical cannabinoid ingredient remaining within at least about 90 to about 110 percent of its original amount included in the dosage form for at least 1 year, and preferably for at least about 18 months after manufacture.

In certain embodiments, the cannabinoid formulations of the invention comprise effective amounts of one or more stabilizers to promote stability of the cannabinoid against unacceptable degradation. The stabilizers may comprise one or more anti-oxidants, one or more organic bases, and/or other stabilizers for cannabinoids known to those skilled in the art. In certain preferred embodiments, the stabilizer comprises butylated hydroxyanisole (BHA) or butylated hydroxytoluene (BHT) or any combination thereof.

The invention is further directed in part to a method for stabilizing a dosage form containing a cannabinoid as the active pharmaceutical ingredient, comprising dissolving a therapeutically effective amount of the cannabinoid in a mixture of aqueous and organic carriers. In certain embodiments, the carrier comprises buffering agents. In certain embodiments, the carrier further comprises one or more stabilizers for the cannabinoid (e.g, anti-oxidants, organic bases, or both, as set forth more specifically herein).

In certain embodiments, the carrier further contains an effective amount of a viscosity modifier that may be included to provide a pharmaceutically acceptable viscosity to the cannabinoid dispersed in the carrier.

In certain preferred embodiments where the stabilizer comprises an organic base, the dosage form may comprise from about 0.001% w/w to about 5% organic base, preferably from about 0.001% w/w to about 0.5% w/w organic base, by volume. In certain preferred embodiments, the organic base is selected from the group consisting of butylated hydroxyanisole (BHA), butylated hydroxytoluene (BHT), ascorbic acid, sodium ascorbate, ascorbyl palmitate and any combination of the foregoing.

The anti-oxidant included in the formulations of the invention may further be selected from e.g., propyl gallate, lecithin, Vitamin E tocopherol, sesamin, sesamol, sesamolin, alpha tocopherol, ascorbic acid, ascorbyl palmitate, fumaric acid, malic acid, and sodium metabisulphite, disodium ethylenediaminetetracetic acid (EDTA), and combinations of any of the foregoing.

The formulations of the present invention comprise a cannabinoid concentration range of from about 0.01 to about 20 mg/ml. In certain embodiments, the formulations of the invention comprise a cannabinoid in a concentration from about 1 to about 10 mg/ml. In certain other embodiments, the formulations of the present invention comprise a cannabinoid in a formulation of about 5 mg/ml.

In certain preferred embodiments, the dosage forms of the invention comprises from about 0.05% to about 90% cannabinoid, preferably from about 0.1% to about 50% cannabinoid, more preferably about 0.1 to about 10% w/w cannabinoid, and most preferably from about 0.1% to about 5% cannabinoid, by weight.

In accordance with any of the above objects, it is a further object of the invention to provide stabilized cannabinoid formulations where, the carrier is buffered to a pH of from about 5 to about 10. In certain other embodiments, the carrier is buffered to a pH of from about 6 to about 8. In accordance with any of the above objects, the formulations of the invention are preferably buffered to a pH of from about 6.5 to about 7.5.

In certain embodiments wherein the formulation is a solution for oral administration, the mixture preferably contains from about 15% to about 65% w/w ethanol, from about 0% to about 40% w/w water, from about 5 to about 50% propylene glycol and from about 0% to about 50% polyethylene glycol (PEG400). In certain preferred embodiments the aqueous-based oral solution dronabinol formulations also contain a pharmaceutically acceptable sweetener such as sucralose, sucrose, sorbitol and fructose in an amount from about 0.05% to about 10% by weight.

The formulations in accordance with any of the above objects may also include sweeteners such as xylitol from about 5% to about 25%; saccharin from about 0.01% to about 5%; and saccharin sodium from about 0.01% to about 5% by weight of the formulation.

The invention is further directed to a dosage form which further comprises one or more additional therapeutically active agents. Non-limiting examples of such additional therapeutically active agents include a narcotic analgesic, a non-narcotic analgesic, an anti-emetic, a steroid, and mixtures of any of the foregoing.

In certain embodiments, formulations of the invention include further pharmaceutically acceptable excipients. Non-limiting examples of such pharmaceutically acceptable excipients include solubilizers for said cannabinoid, emulsifiers, absorption enhancers, surfactants, propellants, etc.

For purposes of the present invention the terms droplets and particles may be used interchangeably.

The term "pharmaceutically acceptable" is defined for purposes of the invention as meaning that a particular ingredient (e.g., pharmaceutical carrier, excipient) is not biologically or otherwise undesirable in an oral dosage form, i.e., the amount of the compound in an orally administered composition or dosage form does not cause any undesirable effects to the formulation or to the patient.

Testing for stability may be conducted, (e.g., for eighteen months stability determination) by placing the dosage forms of the present invention under storage conditions selected from the group consisting of (i) 2-8° C., (ii) 25° C./60% relative humidity (RH) for 6-24 months; (iii) 30° C./65% relative humidity (RH) for 6-12 months; (iv) 40° C./75% relative humidity (RH) for 3-6 months; and (v) any combination thereof.

The phrase "does not degrade to an unacceptable extent" and the term "stable" as it applies to the cannabinoid formulations of the invention is meant for purposes of the invention to mean that the formulation contains at least about 80% w/w, and preferably at least about 90% w/w of the cannabinoid in undegraded form after exposure of the formulation to storage conditions selected from the group consisting of (i) 2-8° C., (ii) 25° C./60% RH for 6-24 months; (iii) 30° C./65% RH for 6-12 months; (iv) 40° C./75% RH for 3-6 months; and (v) any combination thereof. In preferred embodiments, the phrase "does not degrade to an unacceptable extent" means that the active pharmaceutically acceptable cannabinoid ingredient (e.g., dronabinol) contained within the dosage form is maintained preferably between 90-110% of its initial (incorporated) amount during the desired (e.g., labeled) shelf-life of the dosage form (e.g., a minimum of 18 months after the date of manufacture of the dosage form).

For purposes of the invention, the term "dispersed" as it is used to describe the presence of the cannabinoid in the pharmaceutically acceptable carrier, is meant to encompass a mixture of the cannabinoid and the pharmaceutically acceptable carrier in which the cannabinoid is completely or partially dissolved therein, or the cannabinoid is partially or completely in solid particulate form therein.

For purposes of the invention, the term "unacceptable degradation" means degradation of the cannabinoid within the dosage form to an extent which will cause the dosage form to have cannabinoid in the dosage form at a level outside the acceptable ranges set forth herein, and/or which cause the formulation to include cannabinoid degradants at levels which exceed the amounts specified herein, and/or which cause the formulation to not meet its label claim for shelf life. In certain preferred embodiments, the cannabinoid formulations of the invention are deemed stable as per the FDA guidance for at least 18-months expiration dating.

For purposes of the present invention, the term "Cmax" means maximum plasma concentration. The term "Tmax" means the time to reach the maximum concentration and "AUC" means area under the curve.

For the purposes of the present invention, it shall be understood that whenever a reference is made to a pharmacokinetic value (e.g., mean Cmax, median Tmax, mean AUC, etc.), that value is considered to encompass values that would provide a bioequivalent result as determined by a regulatory authority such as the U.S. Food and Drug Administration.

In accordance with any of the above objects, the invention is also directed to a formulation that provides more consistent in vivo absorption, more convenient dosing and/or improved dose flexibility as compared to a soft gelatin dronabinol capsule formulation.

In accordance with any of the above objects, the invention is further directed to a formulation that is physically stable at room or refrigerated temperatures. In still other embodiments, the formulations are chemically stable at room or refrigerated temperatures.

DETAILED DESCRIPTION

Lipophilic compounds that are unstable in the presence of oxygen and moisture, such as cannabinoids, have proven difficult to formulate into stable aqueous-based formulations due to degradation and insolubility. It has been reported that when the water content of liquid dronabinol formulations increases and the amount of organic solvent such as ethanol decreases, the drug readily falls out of solution, thus inducing instability (Dedhiya et al., 2004).

The instability of prior art soft gelatin capsule dronabinol formulations has been overcome by virtue of the present invention which also has an improved in vivo absorption profile. In certain embodiments, the present invention (i) provides methods and formulations which provide formulations having an aqueous-based component, but that are nonetheless stable; (ii) provides methods and formulations which include anti-oxidants and/or preservatives in effective amounts to substantially prevent or slow the degradation and physical instability of the dronabinol or cannabinoid in the formulation; (iii) provides methods and formulations which enhance the in vivo absorption profile of dronabinol over soft gelatin capsule dronabinol formulations; (iv) provides methods and formulations with more convenient dosing and/or improved dose flexibility; (v) provides methods and formulations with faster onset of dronabinol in vivo absorption and lower inter-subject variability of plasma THC levels; (vi) provides methods and formulations with dronabinol that have an equivalent or better safety profile than soft gelatin capsule dronabinol formulations; or any combination of (i)-(vi) above.

Cannabinoids

Although certain sections of this specification provide specific focus on dronabinol, one skilled in the art will appreciate that the present invention is applicable to the class of pharmaceutically acceptable cannabinoids. For purposes of the present invention, the term "cannabinoid" includes naturally occurring and non-natural derivatives of cannabinoids which can be obtained by derivation of natural cannabinoids and which are unstable like natural cannabinoids. In other words, the cannabinoid used in the formulations of the invention may be natural, semi-synthetic, or synthetic. The cannabinoid may be included in its free form, or in the form of a salt; an acid addition salt of an ester; an amide; an enantiomer; an isomer; a tautomer; a prodrug; a derivative of an active agent of the present invention; different isomeric forms (for example, enantiomers and diastereoisomers), both in pure form and in admixture, including racemic mixtures; enol forms. The term "cannabinoid" is also meant to encompass derivatives that are produced from another compound of similar structure by the replacement of, e.g., substitution of one atom, molecule or group by another such as 11-hydroxy-delta-8-tetrahydrocannabinol and 11-hydroxy-delta-9-tetrahydrocannabinol. The term "cannabinoid", as used in the present invention, further includes delta-8-tetrahydrocannabinol, delta-9-tetrahydrocannabinol, cannabidiol, cannabinol, cannabigerol, nabilone, delta-9-tetrahydro cannabinotic acid, the non-psychotropic cannabinoid 3-dimethylnepty 11 carboxylic acid homologine 8. (J. Med. Chem. 35, 3135, 1992). The term cannabinoid also includes prodrugs of cannabinoids, as well as pharmaceutically acceptable salts and complexes of cannabinoids. An example of a suitable prodrug is THC-hemisuccinate.

The term "cannabinoid" is further meant to encompass natural cannabinoids that have been purified or modified, and synthetically derived cannabinoids, for example, United States Patent Application Publication 2005/0266108, hereby incorporated by reference in its entirety, describes a method of purifying cannabinoids obtained from plant material. The term cannabinoid is also meant to include the compounds described in U.S. Pat. No. 6,713,048, including levonantradol, (−)-HU-210, Win 55212-2, Anandamide, Methandamide, CP 55940, O-1057, SR 141716A, etc. The disclosure of this patent is hereby incorporated by reference in its entirety.

In certain preferred embodiments of the present invention, the active ingredient (cannabinoid) comprises or consists essentially of Delta-9-tetrahydrocannabinol, also known as (and referred to herein as) dronabinol. Dronabinol is naturally-occurring and has been extracted from Cannabis sativa L. (marijuana). It has also been produced chemically as described in U.S. Pat. No. 3,668,224. Dronabinol is a light-yellow resinous oil that is sticky at room temperature, but hardens upon refrigeration. It turns to a flowable liquid when heated at higher temperatures. Dronabinol is insoluble in water. It has a pKa of 10.6 and an octanol-water partition coefficient: 6,000:1 at pH 7. Dronabinol is available in natural (extracted from plant) and synthetic forms. On the other hand, synthetic dronabinol may be utilized and may be synthesized using the starting materials Olivetol and p-2,8-menthadien-2-ol (PMD).

The term "dronabinol" is further meant to encompass naturally occurring dronabinol, metabolites, synthetically derived dronabinol, and synthetically modified dronabinol starting with a molecule obtained from a natural source for example, United States Patent Application Publication 2005/0171361, hereby incorporated by reference in its entirety, describes a method of extracting delta-9-THC acid from the plant material by chromatography and then synthetically converting it to dronabinol.

In certain preferred embodiments of the invention, the cannabinoid used in the formulation is esterified. Esterified forms of THC are described in U.S. Pat. No. 4,933,368 and in U.S. Pat. No. 5,389,375. Other useful polar esters are the hemi-ester of malonic acid and the alaninate ester of alanine. It has been reported, e.g., in U.S. Pat. Nos. 5,508,051 and 5,389,375, that salts of the terminal carboxylic acid group of the ester, for example, the N-methyl glutamine salt as well as the sodium and potassium salts are also useful. The descriptions of U.S. Pat. Nos. 4,933,368; 5,508,037; and 5,389,375, are incorporated herein by reference. These ester compounds are hydrolyzed in the blood stream releasing THC to provide a high degree of bioavailability of THC without regard to patient conditions and anomalies.

Oral THC is known to possess erratic in vivo absorption from the gastrointestinal tract, is subject to the first-pass effect resulting in heavy metabolism with production of high levels of 11-OH-delta-9-THC. It is reported that this 11-hydroxy metabolite is more potent agonist than delta-9-THC. The pro-drug THC hemisuccinate (THC-HS) has been formulated in a suppository base in order to avoid this problem, as described in U.S. Pat. Nos. 5,508,037 and 5,389,375, both of which are hereby incorporated by reference.

THC obtained by any means can be esterified by the reaction of THC with an organic acid, an organic acid halide or preferably organic acid anhydride in the presence of 4-amino-substituted pyridine alone or in admixture with an organic amine, or in any other manner known to those skilled in the art. U.S. Pat. No. 6,008,383 (Elsohly, et al.), hereby incorporated by reference, describes a process for converting dronabinol to a variety of ester analogs, which process is said to be economical and efficient. Therein, dronabinol is esterified by reaction with a carboxylic acid, an acid halide or an acid anhydride in the presence of a 4-aminopyridine either alone or in admixture with an organic amine such as a mono-, di-, or tri-alkyl amine.

In certain exemplary embodiments, the cannabinoid comprises dronabinol hemisuccinate ester (THC-HS).

Formulations

Cannabinoids in general, and dronabinol specifically, are insoluble in water. The formulations of the present invention, therefore, preferably include one or more pharmaceutically acceptable co-solvents for the cannabinoid. The organic co-solvent will be present in an amount effective to have the cannabinoids substantially solubilized in the formulation.

Therefore, the amount of organic solvent in the formulation will vary based on the concentration of the cannabinoid. The amount of organic co-solvent will also vary based on the partition coefficient of the particular cannabinoid molecule.

Solvents/Co-Solvents

In certain embodiments, the solvents are organic solvents such as dehydrated alcohol, ethanol, propanol, isopropanol, propylene glycol, polyethylene glycol, and combinations thereof that are pharmaceutically acceptable based on the desired formulation. For purposes of this invention, the term "dehydrated alcohol" is used interchangeably with the term "absolute alcohol". The amount of dehydrated alcohol in a particular formulation will vary based on the intended formulation and the solubility of the cannabinoid. The amount of dehydrated alcohol in the formulations of the present invention can range from about 10% to about 90%; from about 15% to about 65%; and about 15% to about 50% by weight.

In certain preferred embodiments, polyethylene glycol is used as a portion of the co-solvent for the cannabinoid, more preferably a low molecular weight polyethylene glycol is used, most preferably polyethylene glycol (PEG) 400.

In certain embodiments, the polyethylene glycol comprises from about 0% to about 50% by weight of the oral aqueous-based dronabinol formulation and preferably from about 0% to about 15% by weight of the oral aqueous-based dronabinol formulation.

In certain embodiments, the formulation contains another co-solvent from about 0% to about 50% by weight propylene glycol and preferably from about 1% to about 10% by weight propylene glycol. Most preferably, the solvent and co-solvents will range from a total of about 66-74% by weight.

Solubilizing Agents

In certain embodiments of the invention further solubilizing agents are included in the formulation. Exemplary solubilizing agents include Capryol 90; Cremophor RH40; Labrafil M 1944 CS; Labrafil M 2125 CS; Lauroglycol 90; PEG MW>4000; Plurol Oleique CC 497; poloxamer 124; poloxamer 188; Softigen 701; Softigen 767; Tagat TO; Tween 80; triacetin; triethylcitrate; tributylcitrate; acetyl triethylcitrate; acetyl tributyl citrate; ethyl oleate; ethyl caprylate; ethyl butyrate; triacetin; 2-pyrrolidone; 2-piperidone; N-methylpyrrolidone; N-ethylpyrrolidone; N-hydroxyethyl pyrrolidone; N-octylpyrrolidone; N-laurylpyrrolidone; dimethylacetamide; Miglyol, lanolin, petrolatum, mineral oil and mixtures thereof. The formulations of the present invention may comprise a solubilizing agent from about 0.1% to about 100% of the inactive ingredients or from about 5% to about 85% by weight.

Other components such as preservatives, antioxidants, surfactants, absorption enhancers, viscosity modifiers, bulking agents, diluents, coloring agents, flavoring agents, pH modifiers, sweeteners or taste-masking agents may also be incorporated into any of the compositions described as part of the invention. The amount of each of these components which may be used will be optimized for each formulation, in order to obtain a stable product (dosage form) having the desired shelf-life. Generally speaking, in embodiments in which these components are included, suitable formulations may include from about 0.001% to about 20% w/w of a pharmaceutically acceptable preservative, antioxidant, surfactant, absorption enhancer, viscosity modifier, bulking agent, diluent, coloring agent, flavoring agent, pH modifier, sweetener or taste-masking agent.

Stabilizer

In certain preferred embodiments, the formulation contains amounts of one or more pharmaceutically acceptable anti-oxidants in an amount effective to stabilize the cannabinoid contained therein such that the cannabinoid does not degrade to an unacceptable extent and the formulation is deemed stable for at least eighteen months when placed under storage conditions selected from refrigerated or room temperature.

In further embodiments of the invention, an effective (stabilizing) amount of one or more pharmaceutically acceptable anti-oxidants is added to the formulation. The term "anti-oxidant" is used herein to describe any compound or combination of compounds that prevents or slows down cannabinoid oxidation. Any of the known anti-oxidants may be used, including but not limited to anti-oxidants such as butylated hydroxyanisole (BHA), butylated hydroxytoluene (BHT), propyl gallate, lecithin, Vitamin E tocopherol, sesamin, sesamol, sesamolin, alpha tocopherol, ascorbic acid, ascorbyl palmitate, fumaric acid, malic acid, sodium ascorbate and sodium metabisulphite, as well as chelating agents such as disodium EDTA, may also be used to stabilize the cannabinoid formulations of the present invention.

The preparation may also contain anti-oxidant synergists to prevent oxidative degradation. Any of the known anti-oxidant synergists may also be used in effective amounts, for example disodium edetate.

The amount of anti-oxidant which may be used will be optimized for each formulation, in order to obtain a stable product (dosage form) having the desired shelf-life. Generally speaking, in embodiments in which an anti-oxidant is included, suitable formulations may include from about 0.001% to about 20% w/w of a pharmaceutically acceptable anti-oxidant(s). In other preferred embodiments, BHA, or BHT or combinations thereof, is used as the anti-oxidant in an amount of from about 0.001 to about 1%, w/w, and in certain embodiments more preferably in the range from about 0.01% to about 0.1% w/w. The anti-oxidant preferably prevents the formation of degradants in the dosage form such as those mentioned above, namely cannabinol (CBN), cannabidiol (CBD), or dihydrocannabinol to unacceptable levels (e.g., as previously specified herein).

Bases

In further embodiments of the invention, effective amounts of one or more pharmaceutically acceptable organic or inorganic bases are added to the cannabinoid formulation in order to stabilize the cannabinoid from undesirable levels of degradation. Examples of suitable organic bases which may be effectively used in the cannabinoid formulations of the present invention include but are not limited to any pharmaceutically acceptable primary, secondary and tertiary organic amines which are GRAS ingredients (generally regarded as safe), such as methanolamine, ethanolamine, meglumine, other alkylamines (e.g. di-alkyl amines and tri-alkyl amines), and any combination thereof. In embodiments of the present invention where organic bases are included, suitable formulations may include from about 0.001% to about 20% w/w of organic base(s).

In certain preferred embodiments, the amount of organic base(s) in the formulation is from about 0.001% w/w to about 5% w/w, and more preferably from about 0.005% w/w to about 2% w/w. In other preferred embodiments, the formulations include stabilizing amounts of both one or more anti-oxidants and one or more base.

In certain other embodiments, the formulations in accordance with the present invention are stabilized with an inorganic base e.g, NaOH, or MgOH. Generally, in embodiments in which these components are included, suitable formulations may include from about 0.001% to about 20% w/w of a pharmaceutically acceptable inorganic base.

Preservatives

Preservatives have bactericidal and fungicidal properties. Parabens are widely used preservatives in the pharmaceutical industry because of their efficacy as preservatives in combination with their long history of safe use. Parabens work best when they are used in combination since various combinations of parabens allows for the use of lower levels while increasing preservative activity. Examples of parabens include methyl paraben and propyl paraben. In one exemplary embodiment, the oral formulation of the present invention may include 0.001% to 0.1% by weight of methyl paraben and/or 0.001% to 0.1% by weight propyl paraben.

Buffers

In addition the formulations may additionally include physiologically acceptable components such as sodium chloride and like materials conventionally used to achieve isotonicity with typical body fluids. Agents which buffer the pH to maintain a physiologically compatible pH range to enhance the solubility and stability of the active agent present, and the like may also be included in certain embodiments of the present invention.

Suitable buffers include, but are not limited to acetate, bicarbonate, citrate, phosphate, pharmaceutically acceptable salts thereof and combinations or mixtures thereof. When one or more buffers are utilized in the formulations of the invention, they may be combined, e.g., with a pharmaceutically acceptable vehicle and may be present in the final formulation, e.g., in an amount ranging from about 0.1% to about 20% by weight, more preferably from about 0.5% to about 10% by weight. Therefore, from about 5 mM to about 200 mM concentration of a buffer may be present in the formulations. The concentration of buffer is such that a pH of the formulation is from about 5 to about 10; preferably from about 6 to about 8; more preferably from about 6.5 to about 7.5 and most preferably about 7.

In certain other embodiments, the formulations may be isotonic. Isotonic formulations may be provided by the addition of a tonicity agent. Suitable tonicity agents include, but are not limited to any pharmaceutically acceptable sugar, salt or any combinations or mixtures thereof, such as, but not limited to dextrose and sodium chloride. The tonicity agents may be present in an amount from about 100 mOsm/kg to about 500 mOsm/kg. In certain preferred embodiments, the tonicity agent is present in an amount from about 200 mOsm/kg to about 400 mOsm/kg and more preferably from about 280 mOsm/kg to about 320 mOsm/kg.

Sweeteners

In some embodiments, the invention is directed to stable aqueous-based cannabinoid formulations for oral administration that contain sucrose, fructose, sucralose, sorbitol, xylitol, saccharin, saccharin sodium, or combinations thereof as a sweetening agent. In certain exemplary embodiments, the aqueous-based oral dronabinol formulations contain a pharmaceutically acceptable sweetener such as sucralose in an amount from about 0.01% to about 10% by weight. Other exemplary embodiments may include sweeteners such as xylitol from about 1% to about 25%, saccharin from about 0.01% to about 5%, and saccharin sodium from about 0.01% to about 5% by weight of the formulation.

Viscosity Modifiers

In further embodiments, the invention is directed to formulations that further contain viscosity modifiers including, for example, cellulose or cellulose derivatives such as ethylcellulose, hydroxyethylcellulose, hydroxypropylcellulose, caboxymethylcellulose, sodium hydroxypropylmethylcellulose, methylcellulose, methylethylcellulose, sodium carboxymethylcellulose, Aerosil (silicon dioxide), cetostearyl alcohol, cetyl alcohol, stearyl alcohol, Gelucires 33/01, 39/01 and 43/01, glyceryl behenate (Compritol 888 A TO), glyceryl palmitostearate (Precirol AT05), Softisans 100, 142, 378 and 649, stearyl alcohol carbomer, xanthan gum, maltodextrin, acacia, tragacanth, povidone and polyvinyl alcohol.

Absorption Enhancers

Absorption enhancers for use in accordance with certain embodiments of the present invention include, for example, Gelucire 44/14; Gelucire 50/13; Tagat TO; Tween 80; isopropyl myristate, polysorbates, sorbitan esters, poloxamer block copolymers, PEG-35 castor oil, PEG-40 hydrogenated castor oil, caprylocaproyl macrogol-8 glycerides, PEG-8 caprylic/capric glycerides, sodium lauryl sulfate, dioctyl sulfosuccinate, polyethylene lauryl ether, ethoxydiglycol, propylene glycol mono-di-caprylate, glycerol monocaprylate, glyceryl fatty acids (C8-C18) ethoxylated, oleic acid, linoleic acid, glyceryl caprylate/caprate, glyceryl monooleate, glyceryl monolaurate, caprylic/capric triglycerides, ethoxylated nonylphenols, PEG-(8-50) stearates, olive oil PEG-6 esters, triolein PEG-6 esters, lecithin, d-alpha tocopheryl polyethylene glycol 1000 succinate, polycarbonate, sodium glycocholate, sodium taurocholate, cyclodextrins, citric acid, sodium citrate, triacetin, combinations thereof, and the like. In certain preferred embodiments, the absorption enhancer is triacetin. In certain preferred embodiments wherein an absorption enhancer is included in the formulation, the absorption enhancer is included in an amount of from about 0.001% to about 10% by weight of the formulation, preferably in an amount of about 0.01% to about 5% by weight of the formulation.

Bulking Agents

Bulking agents may also be used in accordance with certain embodiments of the present invention including for example, microcrystalline cellulose, mannitol, xylitol, starches and the like. In certain preferred embodiments, the bulking agent is mannitol. In certain preferred embodiments wherein bulking agent is included in the formulation, the bulking agent is included in an amount of from about 0.001% to about 10% by weight of the formulation, preferably in an amount of about 0.01% to about 5% by weight of the formulation.

Gelling Agents

The formulations of the present invention also may contain suitable gelling or suspension agents include carbomers such as Carbopol, modified cellulose derivatives, naturally-occurring, synthetic or semi-synthetic gums such as xanthan gum, acacia and tragacanth, modified starches, co-polymers such as those formed between maleic anhydride and methyl vinyl ether, colloidal silica and methacrylate derivatives sold under the trade name Eudragit™, or a mixture thereof.

In further embodiments, additional excipients compatible with the formulations of the invention may be incorporated into the liquid drug formulation, if needed, such as known surfactants (e.g. Capryol 90; Cremophor RH40; Gelucire 44/14; Gelucire 50/13; Imwitor 91; Imwitor 308; Imwitor 380; Imwitor 742; Imwitor 780K; Imwitor 928; Imwitor 988; Labrafil M 1944 CS; Labrafil M 2125 CS; Lauroglycol 90; Tagat TO; Tween 80; and mixtures thereof); and emulsifiers (e.g., Gelucire 44/14; Gelucire 50/13; Imwitor 91; Imwitor 308; Imwitor 380; Imwitor 742; Imwitor 780K; Imwitor 928; Imwitor 988; poloxamer 124; poloxamer 188; Tagat TO; Tween 80; lecithin; lysolecithin; phosphatidylcholine; phosphatidylethanolamine; phosphatidylglycerol; phosphatidic acid; phosphatidylserine; lysophosphatidylcholine; lysophosphatidylethanolamine; lysophosphatidylglycerol; lysophosphatidic acid; lysophosphatidylserine; PEG-phosphatidylethanolamine; PVP-phosphatidylethanolamine; sodium lauryl sulfate and mixtures thereof).

Other additives conventionally used in pharmaceutical compositions can be included, and these additives are well known in the art. Such additives include pharmaceutically acceptable detackifiers, anti-foaming agents, chelating agents, viscomodulators, tonicifiers, flavorants, colorants odorants, opacifiers, suspending agents, binders, fillers, plasticizers, lubricants, and mixtures thereof. The amounts of such additives can be readily determined by one skilled in the art, according to the particular properties desired, keeping in mind the possibility that any such additives should preferably not negatively impact the stability of the final formulation.

Suitable coloring agents include red, black and yellow iron oxides and FD&C dyes such as FD&C Blue No. 2, FD&C Red No. 40, and the like. Suitable flavoring agents include mint, raspberry, licorice, orange, lemon, grapefruit, caramel, vanilla, cherry grape flavors, combinations thereof, and the like. Suitable sweeteners include sucralose, xylitol, saccharin, and the like. Suitable pH modifiers include citric acid, tartaric acid, phosphoric acid, hydrochloric acid, maleic acid, sodium hydroxide, and the like. Suitable sweeteners include aspartame, acesulfame K, thaumatic, and the like. Suitable taste-masking agents include sodium bicarbonate, ion-exchange resins, cyclodextrin inclusion compounds, adsorbates, and the like.

It is recognized that pharmaceutical excipients may perform more than one function, and are therefore characterized as having different uses depending on the particular application. While the use of an excipient in the context of a particular formulation may determine the function of the excipient, the inclusion of any particular excipient into any one or more category as set forth above is not meant to limit the function of that excipient.

Although the ingredients of the formulations of the present invention are characterized herein as percentage based on weight, one skilled in the art will appreciate that scaled-up versions of the formulations specifically described herein may be characterized instead on a volume percentage basis. Where the density of a particular component is 1 g/ml the amount of the component based on volume and weight will be the same. Where the density deviates from 1 g/ml, the amounts based on weight or volume will differ accordingly.

Additional Drugs

Cannabinoids such as dronabinol may be used alone or in combination with other cannabinoids or *cannabis*-derived molecules (synthetic or natural) or other medications. Those skilled in the art will readily recognize that, for example, in the case of AIDS wasting syndrome, the patient will likely also be taking drugs that combat the AIDS virus. Similarly, those skilled in the art will readily recognize that patients receiving chemotherapy for cancer may also receive other antiemetics, and cancer patients seeking to relieve pain are likely to receive opioids as well as nonsteroidal anti-inflammatory agents. The formulations and methods of the invention may further include one or more additional therapeutically active agents, such as, for example, non-narcotic analgesics such as acetaminophen or aspirin, opioid or opiate analgesics, non-steroidal anti-inflammatory drugs (NSAIDs, for example, non-selective cyclooxygenase inhibitors and COX-2 inhibitors), anti-emetics (for example, 5-hydroxytryptamine$_3$ (5-HT$_3$) inhibitors such as ondansetron, granisetron, tropisetron, palonosetron, dolasetron, and mirtazapine) and steroids (for example megestrol acetate, oxandrolone, oxymetholone, and dexamethasone). In certain embodiments of the invention, a second therapeutically active drug including but not limited to the above-mentioned drugs, is incorporated into the oral cannabinoid dosage form. In yet other embodiments, the second therapeutically active drug is separately administered to the patient in conjunction with the oral cannabinoid dosage form. The sequence in which the therapeutic agents are administered is not narrowly critical. "Combination therapy" embraces the administration of the therapeutic agents as described above in further combination with other biologically active ingredients, such as, but not limited to, a pain reliever, such as a steroidal or nonsteroidal anti-inflammatory drug, or an agent for improving stomach motility, for example, and with non-drug therapies, such as, but not limited to, surgery.

The therapeutic compounds that make up the combination therapy may also be administered sequentially, with either therapeutic compound being administered by a regimen calling for two-step administration. Thus, a regimen may call for sequential administration of the therapeutic compounds with spaced-apart administration of the separate, active agents. The time period between the multiple administration steps may range from, for example, a few minutes to several hours to days, depending upon the properties of each therapeutic compound such as potency, solubility, bioavailability, plasma half-life and kinetic profile of the therapeutic compound, as well as depending upon the effect of food ingestion and the age and condition of the subject. Circadian variation of the target molecule concentration may also determine the optimal dose interval.

The therapeutic compounds of the combined therapy whether administered simultaneously, substantially simultaneously, or sequentially, may involve a regimen calling for administration of one therapeutic compound by oral route and another therapeutic compound by an oral route, a percutaneous route, an intravenous route, an intramuscular route, or by direct absorption through mucous membrane tissues. Whether the therapeutic compounds of the combined therapy are administered orally, rectally, topically, buccally, sublingually, or parenterally (for example, subcutaneous, intramuscular, intravenous and intradermal injections, or infusion techniques), separately or together, each such therapeutic compound will be contained in a suitable pharmaceutical formulation of pharmaceutically-acceptable excipients, diluents or other formulations components.

Advantages of the Invention

The branded product MARINOL® (Dronabinol solution in soft gelatin capsules) is highly unstable at room temperature. Therefore the manufacturer of MARINOL® (Unimed Pharmaceuticals Inc.) recommends that the product be stored at refrigerated (2-8.degree. C.) or cool (8-15.degree. C.) conditions (Marinol® package label, Physicians Desk Reference®, Ed. 2003). Also, aqueous-based cannabinoid formulations in the prior art are not considered stable when the aqueous-based component of the carrier exceeds about 20% w/w. At higher concentrations of water, the cannabinoid readily precipitates. Unlike the prior art cannabinoid formulations, the present invention provides a aqueous-based cannabinoid (e.g., dronabinol) formulation drug product that is preferably stable at all conditions—refrigerated, cool and room temperature. In addition, the provided formulations have in vivo absorption variability of less than 50%. Factors contributing to the improved stability, particularly at room temperature, of the present invention include the use of specific solvents/diluents and co-solvents in conjunction with the addition of effective stabilizing amounts of preservatives and antioxidants.

In addition, in certain exemplary embodiments, the cannabinoid formulations of the present invention improve the delivery of the cannabinoid with respect to the extent, rate, and/or consistency of in vivo absorption from the location of administration.

Uses of the Present Invention

The formulations of the present invention are useful in treatment and prevention of a very wide range of disorders, including, for example, nausea, vomiting, anorexia, cachexia, pain, gastrointestinal tract distress (such as heartburn, indigestion, stomachache, sour stomach), inflammatory bowel disease, Crohn's disease, gastritis, irritable bowel syndrome, ulcerative colitis, migraine headaches, postmenstrual syndrome, Alzheimer's dementia, agitation, muscle spasms and other involuntary movement disorders, Parkinson's disease and Parkinsonian-type symptoms, spasticity as result of multiple sclerosis, glaucoma and anxiety disorders. Cannabinoids such as dronabinol have also been reported as showing other biological activities which lend themselves to possible therapeutic applications, such as in the treatment of migraine headaches, spinal cord injury, anxiety, glaucoma and as an analgesic (e.g., to treat neuropathic pain). Cannabinoids such as dronabinol may be used together with opioid analgesics in a synergistic way to relieve pain; advantages of the combination may include decreased administration of opioids (leading to decreased side effects) and may be opioid-sparing (i.e., allowing for a reduced dose of opioid to achieve an equivalent effect). Dronabinol has also been used in the treatment of cancer cachexia (where the loss of appetite induces malnutrition in cancer patients). It has also been used to treat movement disorders including dystonia, Huntington's disease, Parkinson's disease and Tourette's syndrome; epilepsy, and for appetite stimulation in Alzheimer's disease. The use of cannabinoid formulations prepared in accordance with the present invention is contemplated for any and all of the above uses, and any other use known or which become known to those skilled in the art.

Routes of Administration

The formulations of the present invention are preferably administered orally, e.g. via oral solution or sublingually. However, one skilled in the art will appreciate that the stabilized aqueous-based cannabinoid formulations of the present invention are not limited to administration by these routes, and can be administered via the nasogastric route, an intramuscular route, or by direct absorption through mucous membrane tissues, pulmonary, intravenous; transdermal, and ophthalmic administration as well as vaginal, rectal, parenteral or transmucosal (e.g., buccal or sublingual) administration. Thus, the dosage form can be converted from a solution to a suspension, emulsion, suppository, spray, aerosol, gel, drops, syrup, elixir, or other dosage form, as desired.

Oral Solution Formulations

The present invention is formulated into a stable aqueous-based cannabinoid formulation by first preparing a stable aqueous-based formulation in accordance with the present invention, and then further adding a sweetening agent, taste-masking agent, flavoring agent, coloring agent, viscosity modifying agent or combinations thereof.

In accordance with oral solution formulations of the current invention where the cannabinoid is dronabinol, the dronabinol concentration is from about 0.05 mg/ml to about 20 mg/ml; preferably from about 0.5 mg/ml to about 10 mg/ml; and more preferably about 5 mg/ml (or about 0.541% w/w).

The dose of dronabinol provided by the oral solution formulations is preferably from about 2.5 mg to about 20 mg dronabinol.

In certain embodiments, the present invention further contains a viscosity modifying agent, e.g. hydroxypropylcellulose or polyvinylpyrrolidone (povidone or PVP).

In certain embodiments the invention is directed to stable aqueous-based cannabinoid formulations for oral administration that contains sucrose, fructose, sorbitol, xylitol, saccharin, saccharin sodium or combinations thereof as a sweetening agent.

One of skill will readily appreciate that the stable aqueous-based cannabinoid oral liquid formulations of the present invention can be incorporated into any pharmaceutically acceptable single-dose or multi-dose container made from any pharmaceutically acceptable material, (e.g., glass or plastic) to allow for oral dosing of the formulation.

Nebulizer Formulations

Pulmonary administration offers a route of delivery that is suitable for administration of drugs wherein the drug properties make it difficult for oral administration, or where the physical state of the specific patient does not make oral administration desirable (e.g., vomiting, compromised gastrointestinal tract).

In certain embodiments, the formulations of the present invention are designed for pulmonary delivery via a nebulizer. Nebulizers are broadly known to those of skill in the art and the invention is not limited to any specific type of nebulizer.

In certain embodiments, formulations suitable for intrapulmonary administration are administered into the lung as aerosolized particles having a mean mass median aerodynamic diameter in the range of from about 0.01 to about 15 microns. Preferably the created particles have a mean mass median aerodynamic diameter in the range of from about 1 to about 10 microns, more preferably from about 1 to about 5 microns.

Sublingual Formulations

The oral cavity offers a simple, painless method of cannabinoid administration. Within the oral cavity, there are three generally recognized routes of administration of an active agent, namely local, buccal and sublingual.

Local delivery is mainly limited to applications regarding disruptions occurring within the oral cavity itself, such as a canker sore.

The buccal mucosa area encompasses the mucosal membranes of the inner lining of the cheeks. The buccal mucosa is however, less permeable than the sublingual area. One of the major disadvantages associated with buccal mucosa delivery of an active agent has been the relatively low passage of active agents across the mucosal epithelium, thereby resulting in low agent bioavailability, which translates into a substantial loss of usable active agent within each dosage.

Sublingual delivery is achieved through the mucosal membranes lining the floor of the mouth. Because of the high permeability and the rich blood supply, transport via the sublingual route results in rapid in vivo absorption. Sublingual delivery is also beneficial in providing a delivery route appropriate for highly permeable drugs with short delivery period requirements and an infrequent dosing regimen.

The sublingual formulations of the present invention are useful management of anorexia associated with weight loss in patients with AIDS and nausea and vomiting associated with cancer chemotherapy.

Sublingual administration of dronabinol, a pharmaceutically acceptable salt thereof, or derivative thereof, in accordance with the present invention may be particularly beneficial in the patient with cancer who is unable to tolerate oral administration because of nausea and vomiting, dysphagia as a result of disease, or parenteral administration because of decreased venous access, emaciation, or coagulation defects. Sublingual administration of dronabinol in accordance with the present invention preferably has potential advantages of even greater ease of use and rapid onset of appetite stimulant or antiemetic action. Furthermore, because sublingual venous drainage is systemic rather than portal, hepatic first-pass elimination may be avoided. The present invention preferably provides therapeutic formulations and methods for solutions of dronabinol, a pharmaceutically acceptable salt thereof, or derivative thereof to be delivered by sublingual spray pumps.

In certain preferred embodiments, the sublingual administration of dronabinol, a pharmaceutically acceptable salt thereof, or derivative thereof, is advantageous over other forms of administration in that it does not require injection using a syringe and needle, and avoids the need for formulating unit dose oral formulations. Preferably the sublingual administration of dronabinol, a pharmaceutically acceptable salt thereof, or derivative thereof, in accordance with the present invention is suitable for self administration.

In certain embodiments, the formulations of the present invention are advantageous in that propellants such as hydrofluorocarbon propellants such as volatile chlorofluocarbons (e.g. propellant 12), volatile hydrofluoroalkanes (e.g. 1,1,1, 2-tetrafluoroethane and 1,1,1,2,3,3,3-heptafluoro-n-propane) and volatile alkanes (e.g. propane, butane) are not required to deliver the dronabinol, a pharmaceutically acceptable salt thereof, or derivative thereof, sublingually to the patient.

Preferably the formulations of the present invention are delivered as liquid droplets having a mean diameter of at least about 10 microns, preferably at least about 20 microns, more preferably a mean diameter of from about 20 to about 200 microns. Most preferably the formulations are delivered as liquid droplets have a size distribution of from about 5 microns to about 500 microns, preferably from about 10 microns to about 200 microns, preferably from about 20 microns to about 100 microns, more preferably from about 30 microns to about 70 microns.

Preferably the delivery of the formulation of the present invention to the sublingual mucosa via spray results in a rapid in vivo absorption of the dronabinol, a pharmaceutically acceptable salt thereof, or derivative thereof.

In certain embodiments, the formulations of the present invention are designed for sublingual administration.

Intravenous Formulations

Intravenous administration also provides a route of administration where other routes such as oral, pulmonary and sublingual are not desired or suitable. The intravenous route of administration is particularly advantageous where irregular in vivo absorption is a concern. These formulations are prepared in accordance with the procedure used to prepare the above-mentioned solutions. In certain embodiments, the formulations may also contain pH modifiers and or tonicity modifying agents to limit the irritation to the blood vessel upon administration. The formulations are then introduced into an IV infusion bag prior to administration to a patient, either directly or mixed with water prior to being mixed with the solution in the IV infusion bag. The dosage ranges will vary with the choice of cannabinoid.

In certain embodiments, the dose will be adjusted to provide a dose that is therapeutically equivalent to the oral dose of Marinol®. One of skill will appreciate that the dose will typically be lower than the dose delivered through other routes of administration as the intravenous route provides essentially complete bioavailability of the administered dose.

In certain embodiments where the formulation contains dronabinol, the intravenous dose is from about 0.01 mg to about 50 mg.

Ophthalmic Preparations

Ophthalmic administration provides a route of administration where the intended action involves the ocular system. Ophthalmic formulations are prepared in accordance with the procedure described for preparing the above-mentioned formulations. In certain embodiments, the ophthalmic preparations will also contain pH modifiers and or tonicity modifying agents in order to substantially prevention the irritation to the eye upon administration.

In certain other embodiments, the ophthalmic formulations are ointments. In certain other embodiments, the formulations contain lanolin, petrolatum, a high molecular weight glycol, e.g., PEG-400, mineral oil, or combinations thereof. In certain embodiments, the formulations further comprise water.

The ophthalmic formulation may then be transferred into single or multi-dose containers, made from pharmaceutically acceptable materials suitable for ophthalmic administration. The dosage ranges will vary with the choice of cannabinoid. The cannabinoid will be present in a concentration such that a dose will provide a therapeutically effective amount of cannabinoid to treat a condition of the eye, e.g., glaucoma.

In certain embodiments of the invention, the ophthalmic formulation contains dronabinol in a concentration of about 1% by weight. In certain other embodiments, the dosage provides from about 0.01 mg to about 10 mg dronabinol, preferably from about 0.5 mg to about 5 mg, and more preferably from about 1 mg to about 3 mg.

The following examples illustrate various aspects of the present invention, and are set forth to assist in understanding the invention. These examples should not be construed as specifically limiting the invention described and claimed herein. Variations of the invention, including the substitution of all equivalents now known or later developed, which would be within the purview of those skilled in the art, and changes in formulation or minor changes in experimental design, are considered to fall within the scope of the invention and appended claims.

Example 1

Manufacturing Procedure for Aqueous-Based Oral Cannabinoid Solution

The investigational test compound Delta-9-tetrahydrocannabinol (Delta-9-THC) was obtained. All other chemicals used in the formulations were of a pharmaceutical grade. Delta-9-THC (dronabinol) is chemically synthesized as per procedures known to those skilled in the art and is supplied as a clear, amber colored resinous solid at room temperature.

First, a vacuum is applied to the dronabinol before heating. The dronabinol is then liquefied by heating in an oven at 90 degrees C. under vacuum for about sixty (60) to one hundred eighty (180) minutes Next, the liquefied or molten dronabinol is quickly transferred to a separate stock of dehydrated alcohol and the contents are mixed at 50 degrees C.+/−5 degrees C. while being sparged with nitrogen in an airtight container until the dronabinol is completely dissolved in the dehydrated alcohol to create a dronabinol bulk solution that is 6% dronabinol by weight (6% w/w).

An excipient solution is created by dissolving butylated hydroxyl anisole (BHA), sucralose, methyl paraben, and propyl paraben in dehydrated alcohol and sucralose in dehydrated alcohol in an air tight tank/container sparged with nitrogen for about fifteen (15) to thirty (30) minutes. Amounts of PEG 400, propylene glycol, and water are then added while continuing to mix in the air tight tank/container sparged with nitrogen. Next, a calculated amount of dronabinol bulk solution is added to the excipient solution and mixed for about fifteen (15) minutes while continuing to be sparged with nitrogen in an airtight container. An amount of dehydrated alcohol is then added and mixed for about ten (10) minutes while the mixture continues to be sparged with nitrogen in an airtight container to give a final aqueous-based oral dronabinol solution having 0.541% weight dronabinol. The final aqueous-based oral dronabinol solution is then filtered and filled into 30 ml amber glass bottles. Finally, the bottles are manually labeled and placed into labeled cartons.

One exemplary formulation of the cannabinoid solution of the present invention is as follows:

TABLE 1

Aqueous-based Cannabinoid Solution (A)

| Component | Quality Standard | Function | % w/w (Theoretical) |
|---|---|---|---|
| Dronabinol | USP | Active Ingredient | 0.541 (5 mg/mL) |
| Butylated Hydroxy Anisole (BHA) | USP | Antioxidant | 0.01 |
| Sucralose | NF | Sweetener | 0.05 |
| Methyl Paraben | USP | Preservative | 0.02 |
| Propyl Paraben | USP | Preservative | 0.02 |
| PEG 400 | USP | Co-solvent | 12.0 |
| Propylene Glycol | USP | Co-solvent | 5.5 |
| Water | USP | Solvent/Diluent | 31.9 |
| Dehydrated Alcohol | USP | Co-solvent | QS* |
| | | TOTAL | 100 |

*Dehydrated Alcohol content is 50.0% w/w

Pharmacokinetic and Bioavailability Analysis

Protocol was an open-label, 2-treatment, 4-period, 2-sequence, replicate, single-dose, randomized crossover study of the comparative bioavailability of the aqueous-based oral dronabinol solution of the present invention and Marinol 5 mg Capsules (Unimed Pharmaceuticals). Eighty-eight (88) healthy male and female volunteers were randomly assigned to 1 of 2 treatment sequences, Sequence 1 (T→R→T→R) or Sequence 2 (R→T→R→T), where T=the test product, Dronabinol Solution, and R=the reference product, Marinol Capsules.

Eighty-eight (88) subjects were enrolled into the study. Three (3) completed only the first period and no samples were analyzed. One (1) subject completed the first 2 periods, 2 subjects completed 3 of the 4 periods and samples from those periods were analyzed. The analysis population was therefore comprised of 85 subjects, 82 of whom completed all 4 treatments, 2 that completed 3 of the 4 treatments, and 1 that completed 2 of the 4 treatments.

Aqueous-Based Oral Cannabinoid Solution 5 mg/ml

Safety was assessed using the following parameters: physical examinations, vital signs, clinical laboratory evaluations, ECGs, concomitant medication assessments, and adverse event assessments. In addition, subjects were observed for a psychotic episode (e.g. hallucinations, paranoid delusions, personality changes, disorganized thinking) and monitored until their mental status returned to normal while confined to the study site.

Statistical Methods:

Data from 85 subjects who completed the study were included in the pharmacokinetic and statistical analyses.

The following pharmacokinetic parameters were calculated: peak concentration in plasma ($C_{max}$), time to peak concentration ($T_{max}$), elimination rate constant ($\lambda_z$), terminal half-life ($T_{1/2}$), area under the concentration-time curve from time-zero to the time of the last quantifiable concentration ($AUC_{last}$), and area under the plasma concentration time curve from time-zero extrapolated to infinity ($AUC_{inf}$).

Results and Conclusions:

Results of the pharmacokinetic and statistical analyses for the Aqueous-based Oral Cannabinoid Solution (A) of the present invention and the MARINOL® reference product is shown in Table 2. Table 2 shows the pharmacokinetic parameters of dronabinol comparing the Aqueous-based Oral Cannabinoid Solution (Test A) of the present invention and the MARINOL® reference product.

TABLE 2

Summary of PK parameters for dronabinol with replicates combined after oral administration of single 5 mg doses of Dronabinol Solution and Marinol Capsule to healthy volunteers under fasted conditions.

| Parameter* | Test Formulation (A) (Test) | Marinol ® (Reference) |
|---|---|---|
| Cmax (ng/Ml) | 2.4 ± 1.30 (168) | 2.17 ± 1.22 (168) |
| Tmax (h) | 1.00 (168) [0.25-4.00] | 1.00 (168) [0.50-6.00] |
| AUC(0-6) (hxng/Ml) | 3.55 ± 1.63 (168) | 3.19 ± 1.78 (165) |
| AUC(0-12) (hxng/Ml)† | 4.12 ± 1.75 (158) | 4.85 ± 2.08 (74) |
| AUC(0-t) (hxng/Ml) | 4.23 ± 1.97 (168) | 3.56 ± 2.18 (168) |
| AUC(inf) (hxng/Ml) | 4.48 ± 1.94 (150) | 3.48 ± 2.18 (143) |
| $\lambda z$ (h$^{-1}$) | 0.1253 ± 0.0624 (150) | 0.3349 ± 0.1526 (143) |
| t½ (h) | 7.51 ± 5.70 (150) | 3.34 ± 4.46 (143) |

*Arithmetic mean ± standard deviation (N) except Tmax for which the median (N) [Range] is reported.

The time to peak mean dronabinol concentration for the Aqueous-based Oral Cannabinoid Solution of the present invention is shorter than the time to peak mean dronabinol concentration for the MARINOL® reference product. The time to peak mean dronabinol concentration for the Aqueous-based Oral Cannabinoid Solution ranged from about 0.25 hours after administration to about 4.00 hours after administration while the time to peak mean dronabinol concentration for the MARINOL® reference product ranged from about 0.50 hours after administration to about 6.00 hours after administration. With respect to THC levels, pharmacokinetic parameters such as $T_{max}$, $C_{max}$, and AUC show less variability after Aqueous-based Oral Cannabinoid Solution administration compared to the Marinol® reference product. The systemic in vivo absorption of THC is more consistent with the Aqueous-based Oral Cannabinoid Solution of the present invention than it is with the Marinol® reference product. The peak mean dronabinol concentration for the Aqueous-based Oral Cannabinoid Solution of the present invention ranged from about 1.12 ng/ml to about 3.72 ng/ml while the peak mean dronabinol concentration for the MARINOL® reference product ranged from about 0.095 ng/ml to about 3.39 ng/ml.

Stability Data

Table 3 includes stability data for the Aqueous-based Oral Dronabinol Solution of the present invention. The Aqueous-based Oral Dronabinol Solution of the present invention was stored at 5 degrees C., 25 degrees C., and 40 degrees C. and potency and impurities were measured monthly for three months and then at 6 months, 9 months, and 12 months. Percent potency and total impurities were determined by HPLC/UV analysis. As can be seen from the results, the Aqueous-based Oral Dronabinol Solution of the present invention maintained its potency within 3% at all temperatures and total impurities were less than 5%.

TABLE 3

| | Clinical Aqueous-based Oral Solution | | | | | | | |
|---|---|---|---|---|---|---|---|---|
| | 0 Time | | 1 Month | | 2 Month | | 3 Month | |
| Temperature (° C.) | % Potency | % Total Impurities | % Potency | % Total Impurities | % Potency | % Total Impurities | % Potency | % Total Impurities |
| 5 | 100.70 | 1.23 | | | | | 102.20 | 1.25 |
| 25 | 100.70 | 1.23 | | | | | 100.90 | 1.57 |
| 40 | 100.70 | 1.23 | 100.20 | 1.91 | 99.50 | 2.46 | 99.30 | 2.72 |

| | 6 Month | | 9 Month | | 12 Month | |
|---|---|---|---|---|---|---|
| Temperature (° C.) | % Potency | % Total Impurities | % Potency | % Total Impurities | % Potency | % Total Impurities |
| 5 | 101.30 | 1.51 | 101.10 | 1.44 | 100.50 | 1.65 |
| 25 | 100.40 | 2.06 | 100.70 | 2.33 | 98.80 | 2.78 |
| 40 | 97.5 | 4.49 | | | | |

Example 2

Other Exemplary Formulations and Stability Data

Table 4 contains five additional exemplary formulations of the Aqueous-based Oral Dronabinol Solution of the present invention while Tables 5-14 show stability data relating to the respective formulations that demonstrate different combinations of aqueous and organic components that can be used to achieve stable Dronabinol solution.

TABLE 4

| | Oral Solution % w/w | | | | |
|---|---|---|---|---|---|
| COMPONENT | HG026014 | HG026015 | HG026016 | HG026017 | HG026079 |
| Dronabinol | 0.5 | 0.5 | 0.5 | 0.5 | 0.5 |
| BHA | 0.01 | 0.01 | | | 0.01 |
| EDTA | | | 0.1 | 0.1 | |
| Sucralose | | 0.3 | | | 0.05 |
| Cherry flavor | | | | | 0.05 |
| Methyl paraben | | | | | 0.02 |
| Propyl paraben | | | | | 0.02 |
| Glycerine | | | | 50 | |
| Alcohol (deh) | 50 | 50 | 50 | 37 | 49.95 |
| PEG 400 | 12 | 12 | 12 | | 12 |
| Propylene glycol | 5.5 | 5.5 | 5.5 | | 5.5 |
| Phosphate buffer, pH 7 | 31.99 | 31.69 | 31.9 | 12.4 | |
| Water | | | | | 31.9 |

TABLE 5

| | Stability Data HG026014 | | | | | | | | | | | |
|---|---|---|---|---|---|---|---|---|---|---|---|---|
| | 0 Week | | 1 Week | | 2 Week | | 3 Week | | 4 Week | | 6 Week | |
| Temperature (° C.) | % Potency | % Total Impurities | % Potency | % Total Impurities | % Potency | % Total Impurities | % Potency | % Total Impurities | % Potency | % Total Impurities | % Potency | % Total Impurities |
| 25 | 99.54 | 2.21 | | | | | | | 99.23 | 2.04 | | |
| 40 | 99.54 | 2.21 | 97.91 | 2.16 | 97.80 | 2.11 | | | 98.18 | 2.40 | 100.48 | 2.57 |
| 55 | 99.54 | 2.21 | 98.19 | 2.28 | 98.41 | 2.43 | 98.45 | 3.19 | 101.37 | 3.38 | | |

TABLE 6

Stability Data
HG026015

| Temperature (° C.) | 0 Week % Potency | 0 Week % Total Impurities | 1 Week % Potency | 1 Week % Total Impurities | 2 Week % Potency | 2 Week % Total Impurities | 3 Week % Potency | 3 Week % Total Impurities | 4 Week % Potency | 4 Week % Total Impurities | 6 Week % Potency | 6 Week % Total Impurities |
|---|---|---|---|---|---|---|---|---|---|---|---|---|
| 25 | 99.93 | 2.20 | | | | | | | 98.47 | 2.46 | | |
| 40 | 99.93 | 2.20 | 98.07 | 2.42 | 97.50 | 2.26 | | | 98.52 | 2.29 | 99.41 | 2.49 |
| 55 | 99.93 | 2.20 | 97.28 | 2.06 | 97.97 | 2.46 | 96.28 | 3.30 | 99.06 | 3.70 | | |

TABLE 7

Stability Data
HG026016

| Temperature (° C.) | 0 Week % Potency | 0 Week % Total Impurities | 1 Week % Potency | 1 Week % Total Impurities | 2 Week % Potency | 2 Week % Total Impurities | 3 Week % Potency | 3 Week % Total Impurities | 4 Week % Potency | 4 Week % Total Impurities | 6 Week % Potency | 6 Week % Total Impurities |
|---|---|---|---|---|---|---|---|---|---|---|---|---|
| 25 | 99.14 | 2.11 | | | | | | | 99.47 | 1.94 | | |
| 40 | 99.14 | 2.11 | 101.20 | 2.42 | 98.81 | 2.22 | | | 98.84 | 2.20 | 99.53 | 2.58 |
| 55 | 99.14 | 2.11 | 97.66 | 2.26 | 97.46 | 2.74 | 97.68 | 3.18 | 100.25 | 3.61 | | |

TABLE 8

Stability Data
HG026017

| Temperature (° C.) | 0 Week % Potency | 0 Week % Total Impurities | 1 Week % Potency | 1 Week % Total Impurities | 2 Week % Potency | 2 Week % Total Impurities | 3 Week % Potency | 3 Week % Total Impurities | 4 Week % Potency | 4 Week % Total Impurities | 6 Week % Potency | 6 Week % Total Impurities |
|---|---|---|---|---|---|---|---|---|---|---|---|---|
| 25 | 100.06 | 2.00 | | | | | | | 99.70 | 2.17 | | |
| 40 | 100.06 | 2.00 | 100.34 | 2.14 | 97.89 | 2.34 | | | 100.95 | 2.88 | 101.55 | 3.07 |
| 55 | 100.06 | 2.00 | 96.67 | 2.83 | 94.27 | 3.21 | 96.53 | 4.39 | 97.02 | 5.19 | | |

TABLE 9

Stability Data
HG026079

| Temperature (° C.) | 0 Week % Potency | 0 Week % Total Impurities | 1 Week % Potency | 1 Week % Total Impurities | 2 Week % Potency | 2 Week % Total Impurities | 3 Week % Potency | 3 Week % Total Impurities | 4 Week % Potency | 4 Week % Total Impurities | 6 Week % Potency | 6 Week % Total Impurities |
|---|---|---|---|---|---|---|---|---|---|---|---|---|
| 25 | 108.12 | 1.22 | | | | | | | 100.02 | 1.54 | | |
| 40 | 108.12 | 1.22 | | | 103.72 | 2.25 | | | 100.55 | 2.14 | | |
| 55 | 108.12 | 1.22 | 105.38 | 2.11 | 102.46 | 3.11 | 93.10 | 3.65 | 98.12 | 4.89 | | |

Table 10 contains five additional exemplary formulations of the Aqueous-based Oral Dronabinol Solution of the present invention while Tables 11-14 show stability data relating to the respective formulations.

TABLE 10

Formulations

| Component | % w/w AK035144 | % w/w AK035145 | % w/w AK035146 | % w/w AK035147 |
|---|---|---|---|---|
| Dronabinol | 0.541 | 0.541 | 0.541 | 0.541 |
| BHA | 0.01 | 0.01 | 0.01 | — |
| BHT | — | — | 0.01 | — |
| Sucralose | 0.05 | 0.05 | 0.05 | 0.05 |
| Methyl Paraben | — | — | — | — |
| Propyl Paraben | — | — | — | — |
| Dehydrated Alcohol | 50 | 50 | 50 | 50 |
| PEG 400 | 12 | — | 12 | 12 |

TABLE 10-continued

| | Formulations | | | |
|---|---|---|---|---|
| | % w/w | | | |
| Component | AK035144 | AK035145 | AK035146 | AK035147 |
| Propylene glycol | 37.399 | 49.399 | 37.389 | 37.409 |
| Water | — | — | — | — |
| TOTAL | 100 | 100 | 100 | 100 |

TABLE 11

Stability Data AK035144

| Temperature (° C.) | 0 Week | | 1 Week | | 2 Week | | 3 Week | | 4 Week | |
|---|---|---|---|---|---|---|---|---|---|---|
| | % Potency | % Total Impurities | % Potency | % Total Impurities | % Potency | % Total Impurities | % Potency | % Total Impurities | % Potency | % Total Impurities |
| 40 | 113.12 | 1.40 | 108.38 | 2.51 | 107.50 | 2.05 | | | 105.46 | 2.47 |
| 55 | 113.12 | 1.40 | 108.38 | 2.51 | 107.09 | 3.21 | 106.77 | 4.08 | | |

TABLE 12

Stability Data AK035145

| Temperature (° C.) | 0 Week | | 1 Week | | 2 Week | | 3 Week | | 4 Week | |
|---|---|---|---|---|---|---|---|---|---|---|
| | % Potency | % Total Impurities | % Potency | % Total Impurities | % Potency | % Total Impurities | % Potency | % Total Impurities | % Potency | % Total Impurities |
| 40 | 111.24 | 1.47 | | | 104.89 | 1.57 | | | 104.18 | 1.75 |
| 55 | 111.24 | 1.47 | 105.27 | 1.63 | 106.82 | 2.00 | 107.46 | 2.38 | | |

TABLE 13

Stability Data AK035146

| Temperature (° C.) | 0 Week | | 1 Week | | 2 Week | | 3 Week | | 4 Week | |
|---|---|---|---|---|---|---|---|---|---|---|
| | % Potency | % Total Impurities | % Potency | % Total Impurities | % Potency | % Total Impurities | % Potency | % Total Impurities | % Potency | % Total Impurities |
| 40 | 110.19 | 1.47 | | | 104.61 | 1.86 | | | 102.73 | 2.06 |
| 55 | 110.19 | 1.47 | 104.67 | 2.09 | 104.39 | 2.13 | 105.41 | 3.33 | | |

TABLE 14

Stability Data AK035147

| Temperature (° C.) | 0 Week | | 1 Week | | 2 Week | |
|---|---|---|---|---|---|---|
| | % Potency | % Total Impurities | % Potency | % Total Impurities | % Potency | % Total Impurities |
| 40 | 114.03 | 1.42 | | | 106.38 | 3.21 |
| 55 | 114.03 | 1.42 | 104.64 | 5.33 | 101.35 | 8.43 |

It will be understood by those skilled in the art that variations of the component weight percentages of the dronabinol solutions described herein may occur while still achieving the results of a better in vivo absorption profile with faster onset and lower inter-subject availability than prior art soft gelatin capsules containing dronabinol, and enhanced stability and equal or improved safety profiles over prior art soft gelatin capsules containing dronabinol.

Weight percentage ranges of some components for the Dronabinol Solution described may include:

Alcohol: 15-65% w/w

Propylene glycol: 0-50% w/w

Polyethyleneglycol (PEG): 0-50% w/w

Water: 0-40% w/w

Sweetener (e.g., Sucralose): 0-10% w/w, and preferably 0-2% w/w

Anti-oxidants (e.g., BHA, BHT, ascorbyl palmitate, EDTA, lecithin, Vitamin E TPGS, tocopherol etc.): 0-10% w/w, and preferably, 0-2% w/w Preservatives (parabens): 0-5% w/w and preferably, 0-1% w/w

Flavoring agent: 0-5% w/w and preferably, 0-1% w/w

Other agents (e.g., viscosifiers, solubilizers such as surfactants, colorants) can also be included.

Many other variations of the present invention will be apparent to those skilled in the art and are meant to be within the scope of the claims appended hereto. The foregoing specification alludes to beliefs, hypothesis and conclusions of the inventors based on his experience in the field, the reports of others (such as those identified in the publications identified herein), and experiments conducted and reported herein, and are provided for purposes of (possible) explanation only and are not meant to limit the invention in any manner whatsoever.

What is claimed is:

1. An oral pharmaceutical solution consisting essentially of 0.1 to 5% w/w of dronabinol, 25-33% w/w water, 15-65% w/w solvent, a cosolvent consisting of 5.5% w/w propylene glycol and 12% w/w polyethylene glycol, and an excipient selected from the group consisting of butylated hydroxyanisole (BHA), butylated hydroxytoulene (BHT), disodium ethylenediaminetetracetic acid (EDTA), a paraben and a combination thereof wherein said oral pharmaceutical solution is stable for at least eighteen months at room or refrigerated temperatures, has an in vivo absorption variability of less than 50%, and a 5 mg dose of dronabinol provides a pharmacokinetic profile of $C_{max}$ of 2.4+/−1.30 (ng/mL), AUC (0-t) of 4.23+/−1.97 (h*ng/mL) or a $T_{max}$ of 0.25-4.00 (h) following oral administration and wherein the solution is a liquid for oral consumption.

2. The oral pharmaceutical solution of claim 1 consisting essentially of 50% solvent.

3. The oral pharmaceutical solution of claim 2, wherein said solvent is ethanol.

4. The oral pharmaceutical solution of claim 3 in sublingual spray form.

5. An oral pharmaceutical solution consisting essentially of the solution of claim 1 having a 5 mg dose of dronabinol and having a pharmacokinetic profile of $C_{max}$ of 2.4+/−1.30 (ng/mL), AUC (0-t) of 4.23+/−1.97 (h*ng/mL) and a $T_{max}$ of 0.25-4.00 (h).

6. The oral pharmaceutical solution of claim 1 wherein the solution has a pharmacokinetic profile of AUC (inf) of 4.48±1.94 (h*ng/mL) or t½ (h) of 7.51±5.70 or $\lambda z$ ($h^{-1}$) of 0.12353±0.0624 following oral administration.

7. The oral pharmaceutical solution of claim 1 consisting essentially of 5% w/w dronabinol.

8. The oral pharmaceutical solution of claim 1 consisting essentially of 30-33% w/w water.

9. An oral pharmaceutical solution consisting essentially of 5% w/w dronabinol, 12% w/w polyethylene glycol 400, 5.5% w/w propylene glycol, 30-33% w/w water, and 50% w/w alcohol.

10. The oral pharmaceutical solution of claim 1 consisting essentially of 5% w/w dronabinol, 12% w/w polyethylene glycol 400, 5.5% w/w propylene glycol, 30-33% w/w water, 50% w/w alcohol, butylated hydroxyl anisole, sucralose, methyl paraben, and propyl paraben.

11. The oral pharmaceutical solution of claim 1 consisting essentially of 0.01% w/w BHA or EDTA.

12. The oral pharmaceutical solution of claim 1 consisting essentially of 0.05% w/w sweetener.

* * * * *